United States Patent
Jain

(10) Patent No.: US 11,602,533 B2
(45) Date of Patent: Mar. 14, 2023

(54) CRENOLANIB COMBINATION THERAPY

(71) Applicant: Arog Pharmaceuticals, Inc., Dallas, TX (US)

(72) Inventor: Vinay K. Jain, Dallas, TX (US)

(73) Assignee: Arog Pharmaceuticals, Inc., Plano, TX (US)

( * ) Notice: Subject to any disclaimer, the term of this patent is extended or adjusted under 35 U.S.C. 154(b) by 628 days.

(21) Appl. No.: 16/713,935

(22) Filed: Dec. 13, 2019

(65) Prior Publication Data

US 2020/0188385 A1 Jun. 18, 2020

Related U.S. Application Data

(60) Provisional application No. 62/861,424, filed on Jun. 14, 2019, provisional application No. 62/779,128, filed on Dec. 13, 2018.

(51) Int. Cl.
| | |
|---|---|
| *A61K 31/4709* | (2006.01) |
| *A61K 31/50* | (2006.01) |
| *A61K 31/4427* | (2006.01) |
| *A61K 31/415* | (2006.01) |
| *A61P 35/00* | (2006.01) |
| *A61K 45/06* | (2006.01) |

(52) U.S. Cl.
CPC .......... *A61K 31/4709* (2013.01); *A61K 45/06* (2013.01); *A61P 35/00* (2018.01)

(58) Field of Classification Search
CPC ................ A61K 31/4709; A61K 31/50; A61K 31/4427; A61P 35/00
USPC ............................ 514/252.03, 313, 339, 403
See application file for complete search history.

(56) References Cited

U.S. PATENT DOCUMENTS

| | | |
|---|---|---|
| 5,990,146 A | 11/1999 | Boschelli et al. |
| 7,071,337 B2 | 7/2006 | Kath et al. |
| 7,183,414 B2 | 2/2007 | Tom et al. |
| 2013/0230511 A1 | 9/2013 | Heymach et al. |
| 2014/0088143 A1 | 3/2014 | Jain |
| 2015/0111240 A1 | 4/2015 | Wamhoff et al. |
| 2015/0258120 A1 | 9/2015 | Zarnitsyn et al. |
| 2015/0284464 A1 | 10/2015 | Zhu et al. |
| 2016/0235779 A1 | 8/2016 | Marcus |

FOREIGN PATENT DOCUMENTS

| | | |
|---|---|---|
| WO | 1999016755 | 4/1999 |
| WO | 2001040217 A1 | 6/2001 |
| WO | 2017013160 A1 | 1/2017 |

OTHER PUBLICATIONS

Aghajanian et al. "OCEANS: a randomized, double-blind, placebo-controlled phase III trial of chemotherapy with or without bevacizumab in patients with platinum-sensitive recurrent epithelial ovarian, primary peritoneal, or fallopian tube cancer," J Clin Oncol, vol. 30, No. 17, pp. 2039-2045, Jun. 10, 2012.
Anderson, et al. Handbook of clinical drug data, 10th ed. New York ; Toronto: McGraw-Hill Medical Pub Division, 2002, pp. xvii, 1148 p.
Benjamin, et al., "Selective ablation of immature blood vessels in established human tumors follows vascular endothelial growth factor withdrawal," J Clin Invest, vol. 103, No. 2, pp. 159-165, Jan. 1999.
Blackwell, et al. "Circulating D-dimer levels are better predictors of overall survival and disease progression than carcinoembryonic antigen levels in patients with metastatic colorectal carcinoma," Cancer, vol. 101, No. 1, pp. 77-82, Jul. 1, 2004.
Brufsky, et al. "RIBBON-2: a randomized, double-blind, placebo-controlled, phase III trial evaluating the efficacy and safety of bevacizumab in combination with chemotherapy for second-line treatment of human epidermal growth factor receptor 2-negative metastatic breast cancer," J Clin Oncol, vol. 29, No. 32, pp. 4286-4293, Nov. 10, 2011.
Chan, et al., "Bevacizumab in combination with taxanes for the first-line treatment of metastatic breast cancer," Ann Oncol, vol. 21, No. 12, pp. 2305-2315, Dec. 2010.
Erber, et al. "Combined inhibition of VEGF and PDGF signaling enforces tumor vessel regression by interfering with pericyte-mediated endothelial cell survival mechanisms," FASEB J, vol. 18, No. 2, pp. 338-340, Feb. 2004, published online Dec. 4, 2003.
Giantonio et al. "Bevacizumab in combination with oxaliplatin, fluorouracil, and leucovorin (FOLFOX4) for previously treated metastatic colorectal cancer: results from the Eastern Cooperative Oncology Group Study E3200," J Clin Oncol, vol. 25, No. 12, pp. 1539-1544, Apr. 20, 2007.
Gunnarsson, et al. "Evaluating the safety and efficacy of axitinib in the treatment of advanced renal cell carcinoma," Cancer Manag Res, vol. 7, pp. 65-73, 2015.
Holash, et al. "VEGF-Trap: a VEGF blocker with potent antitumor effects" Proc Natl Acad Sci U S A, vol. 99, No. 17, pp. 11393-8, Aug. 20, 2002.
Lehmann, et al. "Adjuvant cisplatin plus methotrexate versus methotrexate, vinblastine, epirubicin, and cisplatin in locally advanced bladder cancer: results of a randomized, multicenter, phase III trial (AUO-AB 05/95)," J Clin Oncol, vol. 23, No. 22, pp. 4963-4974, Aug. 1, 2005.
Michael, et al. "Phase Ib study of CP-868,596, a PDGFR inhibitor, combined with docetaxel with or without axitinib, a VEGFR inhibitor," Br J Cancer, vol. 103, No. 10, pp. 1554-1561, Nov. 9, 2010.
Miles, et al. "Phase III study of bevacizumab plus docetaxel compared with placebo plus docetaxel for the first-line treatment of human epidermal growth factor receptor 2-negative metastatic breast cancer," J Clin Oncol, vol. 28, No. 20, pp. 3239-3247, Jul. 10, 2010.

(Continued)

*Primary Examiner* — Raymond J Henley, III

(74) *Attorney, Agent, or Firm* — Edwin S. Flores; Daniel J. Chalker; Chalker Flores, LLP

(57) ABSTRACT

The present invention includes methods for treating a proliferative disorder by blocking both PDGFR and VEGFR signaling comprising a therapeutically effective amount of crenolanib or salt in combination with a VEGF/VEGFR inhibitor that is not axitinib wherein the crenolanib, VEGF/VEGFR inhibitor that is not axitinib are provided at least one of sequentially or concomitantly, in a subject for use in the treatment of the proliferative disorder, wherein the subject is a human subject.

34 Claims, 2 Drawing Sheets

(56) References Cited

OTHER PUBLICATIONS

Miller, et al. "Paclitaxel plus bevacizumab versus paclitaxel alone for metastatic breast cancer," N Engl J Med, vol. 357, No. 26, pp. 2666-2676, Dec. 27, 2007.

Ogawa, et al. "Clinical significance of platelet derived growth factor-C and -D in gastric cancer," Oncol Lett, vol. 10, No. 6, pp. 3495-3501, Dec. 2015.

Okines, et al. "Bevacizumab with peri-operative epirubicin, cisplatin and capecitabine (ECX) in localised gastro-besophageal adenocarcinoma: a safety report," Ann Oncol, vol. 24, No. 3, pp. 702-709, Mar. 2013.

Perren, et al. "A phase 3 trial of bevacizumab in ovarian cancer" N Engl J Med, vol. 365, No. 26, pp. 2484-2496, Dec. 29, 2011.

Pietras, et al. "Inhibition of PDGF receptor signaling in tumor stroma enhances antitumor effect of chemotherapy," Cancer Res, vol. 62, No. 19, pp. 5476-5484, Oct. 1, 2002.

Pietras, et al. "Inhibition of platelet-derived growth factor receptors reduces interstitial hypertension and increases transcapillary transport in tumors," Cancer Res, vol. 61, No. 7, pp. 2929-2934, Apr. 1, 2001.

Reck, et al. "Phase III trial of cisplatin plus gemcitabine with either placebo or bevacizumab as first-line therapy for nonsquamous non-small-cell lung cancer: AVAil," J Clin Oncol, vol. 27, No. 8, pp. 1227-1234, Mar. 10, 2009.

Robert, et al. "RIBBON-1: randomized, double-blind, placebo-controlled, phase III trial of chemotherapy with or without bevacizumab for first-line treatment of human epidermal growth factor receptor 2-negative, locally recurrent or metastatic breast cancer," J Clin Oncol, vol. 29, No. 10, pp. 1252-1260, Apr. 1, 2011.

Sandler, et al., "Paclitaxel-carboplatin alone or with bevacizumab for non-small-cell lung cancer," N Engl J Med, vol. 355, No. 24, pp. 2542-2550, Dec. 14, 2006.

Tabernero, et al. "Ramucirumab versus placebo in combination with second-line FOLFIRI in patients with metastatic colorectal carcinoma that progressed during or after first-line therapy with bevacizumab, oxaliplatin, and a fluoropyrimidine (RAISE): a randomised, double-blind, multicentre, phase 3 study," Lancet Oncol, vol. 16, No. 5, pp. 199-508, May 2015.

Van Cutsem, et al. "Addition of aflibercept to fluorouracil, leucovorin, and irinotecan improves survival in a phase III randomized trial in patients with metastatic colorectal cancer previously treated with an oxaliplatin-based regimen," J Clin Oncol, vol. 30, No. 28, pp. 3499-3506, Oct. 1, 2012.

Vasudev, et al. "Anti-angiogenic therapy for cancer: current progress, unresolved questions and future directions," Angiogenesis, vol. 17, No. 3, pp. 471-494, Jul. 2014.

Verdaguer, et al. "Ramucirumab in metastatic colorectal cancer: evidence to date and place in therapy," Ther Adv Med Oncol, vol. 8, No. 3, pp. 230-242, May 2016.

United States Patent and Trademark Office, The International Search Report and Written Option for PCT/US2019/066308 dated Mar. 5, 2020, 15 pp.

*Patient alive as of December 2019

CRENOLANIB COMBINATION THERAPY

CROSS-REFERENCE TO RELATED APPLICATIONS

This application claims priority to U.S. Provisional Application Ser. No. 62/779,128, filed Dec. 13, 2018, and U.S. Provisional Application Ser. No. 62/861,424, filed Jun. 14, 2019, the entire contents of each is incorporated herein by reference.

TECHNICAL FIELD OF THE INVENTION

This invention pertains to crenolanib, or salts thereof, and an inhibitor of a Vascular endothelial growth factor (VEGF) and/or a Vascular endothelial growth factor receptor (VEGFR) that is not axitinib (VEGF/VEGFR), for the treatment of proliferative disorders, and to a method of treatment of warm-blooded animals, preferably humans, in which a therapeutically effective dose of crenolanib and a VEGF/VEGFR inhibitor that is not axitinib is administered to a subject suffering from said disease or condition.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with cancer treatments and the use of novel combination therapies that include crenolanib.

On such combination therapy is taught in Michael, et al., "Phase 1b study of CP-868,596, a PDGFR inhibitor, combined with docetaxel with or without axitinib, a VEGFR inhibitor", British Journal of Cancer volume 103, pages 1554-1561 (9 Nov. 2010), which teaches the treatment of cancer patients with CP-868,596 (crenolanib) in combination with a taxane and the VEGF pathway inhibitor axitinib (AG-013736). The combination of crenolanib and axitinib, a VEGFR TKI, along with docetaxel chemotherapy was evaluated in a phase 1b study in patients with relapsed or refractory advanced solid tumors [1]. Tumor types represented in this study that received triplet therapy included non-small cell lung cancer, prostate cancer, oesophageal carcinoma and other solid tumors. Approximately half of these patients had received ≥2 prior chemotherapy regimens. In total, 48 patients in 4 different cohorts were treated: Cohort 1 (7 patients): Crenolanib 60 mg BID plus docetaxel 75 mg/m2; Cohort 2 (25 patients): Crenolanib 100 mg BID plus docetaxel 75 mg/m2; Cohort 3 (7 patients): Crenolanib 100 mg BID plus docetaxel 100 mg/m2; and Cohort 4 (9 patients): Crenolanib 60 mg BID plus docetaxel 75 mg/m2 plus axitinib 5 mg BID. Patients in Cohort 4 who received the triple combination therapy appeared to have an improved outcome compared to patients who received crenolanib with docetaxel alone. Eight of the nine patients (89%) that received the triple combination therapy achieved stable disease (SD) for at least 4½ months, including 1 patient with EG adenocarcinoma; while only 11 of 39 patients (28%) that received only crenolanib plus docetaxel achieved SD. Toxicities of this triplet combination included the known toxicities of each individual agent but also included more mucositis-like symptoms and neutropenia than would have been expected relative to docetaxel alone. As such, the dose of crenolanib was not increased to 100 mg BID, as originally intended. Although toxicities can only be approximately and qualitatively assessed in such a small group, the development of unanticipated toxicities led to the discontinuation of the planned dose escalation and an end to the treatments.

In an earlier study from the same authors, Michael, et al., "Phase 1b study of CP-868,596, a PDGFR inhibitor, in combination with docetaxel (Doc) with or without AG-013736, a VEGF inhibitor" Journal of Clinical Oncology 2008 26:15_suppl, 3549-3549, the authors previously found significant side-effects from the use of crenolanib and AG-013736 (axitinib) included nausea, diarrhea, vomiting, anemia, lethargy, stomatitis, neutropenia, anorexia, peripheral edema and hypertension.

Thus, a need remains for the treatment of cancers with multiple mutations, cancers that become resistant to first line therapies, and/or cancer therapies in which side effects are lessened or reduced.

SUMMARY OF THE INVENTION

In one embodiment, the present invention includes a method for treating a proliferative disorder comprising administering to a subject a therapeutically effective amount of crenolanib or salt thereof in combination with a Vascular endothelial growth factor (VEGF), a Vascular endothelial growth factor receptor (VEGFR), or both (hereinafter the use of the individual agent alone, or in combination, is referred to as VEGF/VEGFR) inhibitor that is not axitinib sufficient to treat the proliferative disorder. In one aspect, the proliferative disorder is at least one of: biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, uterine cancer, or other solid tumors. In another aspect, the therapeutically effective amount of crenolanib is from about 50 mg to 500 mg per day, 100 to 450 mg per day, 200 to 400 mg per day, 300 to 500 mg per day 350 to 500 mg per day, or 400 to 500 mg per day. In another aspect, the therapeutically effective amount of crenolanib is administered at least one of continuously, intermittently, systemically, or locally. In another aspect, the therapeutically effective amount of crenolanib is administered orally, intravenously, or intraperitoneally, and administered up to three times a day for as long as the subject is in need for the treatment of the proliferative disease, which is a time or treatment sufficient to treat the proliferative disease. In another aspect, the crenolanib is crenolanib besylate, crenolanib phosphate, crenolanib lactate, crenolanib hydrochloride, crenolanib citrate, crenolanib acetate, crenolanib toluenesulphonate, and crenolanib succinate.

In another aspect, the method of further comprising providing the subject with a chemotherapeutic agent that comprises one or more of alkylating agents, antimetabolites, natural products, or a combination thereof. In another aspect, the chemotherapeutic agent is an alkylating agent that comprises one or more of carmustine, chlorambucil, cyclophosphamide, ifosfamide, lomustine, streptozotocin, temozolomide, cisplatin, carboplatin, nedaplatin, or oxaliplatin. In another aspect, the alkylating agent therapeutically effective amount is from about 22 mg to 40 mg every 6 weeks, 150 to 200 mg every 6 weeks, 4 to 20 mg per day for 3 to 6 weeks, 2,000 to 4,750 given over 5 days, 4 to 19 mg per day, 1.44 to 3.12 g per day for 5 days in 3 weeks, 150 to 340 mg every 6 weeks, 600 to 1,300 mg per day for 5 days within 6 weeks, 90 to 390 mg daily, 24 to 260 mg per day for 5 days within 6 weeks, 240 to 1,690 mg every 6 weeks, 72 to 234 mg every 4 weeks 78 to 221 mg every 2 weeks. In another aspect, the therapeutically effective amount of the alkylating agent is administered at least one of continuously, intermittently, systemically, or locally. In another aspect, the therapeutically effective amount of the alkylating agent is administered orally, intravenously, subcutaneously, or intraperitoneally. In another aspect, the chemotherapeutic agent is an antimetabolite that comprises one or more of methotrexate, pemetrexed, ralititrexed, fluorouracil, floxuridine, capcitabine, or gemcitabine. In another aspect, the antimetabolite therapeutically effective amount is from about 3.6 to 7.8 mg, 12 to 1,300 mg, 600 to 1,300 mg on day 1 of 21-day cycles. In another aspect, the therapeutically effective amount of the antimetabolite is administered at least one of continuously, intermittently, systemically, or locally. In another aspect, the therapeutically effective amount of the antimetabolite is administered orally, intravenously, subcutaneously, or intraperitoneally. In another aspect, the chemotherapeutic agent is an anti-proliferative agent that comprises one or more of vinblastine, vinorelbine, vincristine, vindesine, vinflunine, paclitaxel, docetaxel, cabazitaxel, etoposide, teniposide, topotecan, irinotecan, doxorubicin, eiprubicin, valrubicin, mitoxantrone, bleomycin, estramustine, or mitomycin. In another aspect, the therapeutically effective amount of the chemotherapeutic agent is from about 0.48 mg to 3.7 mg, 7.2 mg to 28.9 mg, 30 mg to 78 mg, 96 mg to 455 mg, 72 mg to 260 mg, 400 mg to 760 mg every three weeks; 42 to 260 mg given days 1, 3, 5 of 21 day cycle, 198 mg to 650 mg once weekly, 0.9 mg to 3.9 mg daily for 5 days of 21 day cycle, 150 mg to 910 mg daily for 5 days of 21 day cycle, 48 mg to 195 mg every 21 days, 90 mg to 312 mg once every 3 or 4 weeks, 800 mg once weekly every 6 weeks, 14.4 mg to 36.4 mg every 21 days, 12.5 units to 47.5 units every 1 to 2 weeks, 500 mg to 1,520 mg per day, 12 mg to 52 mg every 6 to 8 weeks. In another aspect, the therapeutically effective amount of the chemotherapeutic agent is administered at least one of continuously, intermittently, systemically, or locally. In another aspect, the therapeutically effective amount of the chemotherapeutic agent is administered orally, intravenously, subcutaneously, or intraperitoneally. In another aspect, the VEGF/VEGFR inhibitor that is not axitinib comprises ramicurimab, bevacuzamab, ranizumab, aflibercept, HLX12, ziv-aflibercept, vanucizumab, TX16, UB-922, BEVZ92, BCD-021, BI695502, CHS-5217, JHL1149, FKB238, Abevmy, ONS1045, PF06439535, HD204, SB8, TAB008, RPH001, BP102, HLX04, CT-P16, IBI305, LY01008, Mvasi, apagin, ranibizumab, CHS-3351, PF582, Xlucane, FYB201, razumab, CHS-2020, FYB203, ABP-201, sevacizumab, brolucizumab, CSL346, faricimab, hPV19, TAB014, UB-924, VGX-100, VX70, STI-A0168, CVX-241, BI 836880, ABT-165, conbercept, MP0250, MP0260, angiocal, abicipar pegol, anlotinib, apatinib, altiratinib, vandetanib, linifanib, motesanib, necuparanib, HLX12, APX004, CDP791, HLX-06, IBI302, icrucumab, IMC-1C11, IMC-3C5, MSB0254, navicixizumab, tanibirumab, V-DOS47, cabozantib, brivanib, dovitinib lactate, famitinib, foretinib, fruquintinib, golvatinib, henatinib, ponatinib, lenvatinib, lucitanib, sorafenib, nintedanib, orantinib, pegdinetanib, cediranib, rivoceranib, midostaurin, sitravatinib, regorafenib, sunitinib, sulfatnib, tesevatinib, tivozanib, valatanib, or pazopanib. In another aspect, the therapeutically effective amount of the VEGF/VEGFR inhibitor that is not axitinib is from about 250 mg to 1,425 mg every two to three weeks, 400 mg to 2,600 mg every two to three weeks, 40 mg to 475 mg every two weeks. In another aspect, the therapeutically effective amount of the VEGF/VEGFR inhibitor that is not axitinib is administered at least one of continuously, intermittently, systemically, or locally. In another aspect, the therapeutically effective amount of the VEGF/VEGFR inhibitor that is not axitinib is administered orally, intravenously, subcutaneously, or intraperitoneally. In another aspect, the therapeutically effective amount of at least one of crenolanib, a pharmaceutical agent, and VEGF/VEGFR inhibitor that is not axitinib is administered for as long as the subject needs treatment for the proliferative disease. In another aspect, the therapeutically effective amount is administered one or more times a day or more for as long as the subject is in need of treatment for the proliferative disorder. In another aspect, the therapeutically effective amount of crenolanib is provided in subject with a proliferative disorder. In another aspect, the subject is a patient with a new cancer or the cancer has progressed on at least one line of chemotherapy in the advanced setting.

In another embodiment, the present invention includes a method for dual inhibition of angiogenesis by inhibition of both PDGFR and VEGFR signaling as treatment of a proliferative disorder in a subject comprising a therapeutically effective amount of a VEGF/VEGFR inhibitor that is not axitinib, and crenolanib or pharmaceutically acceptable salt thereof, wherein the subject is a human subject. In one aspect, the proliferative disorder is at least one of: biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, uterine cancer, or other solid tumors. In another aspect, the therapeutically effective amount is from about 50 mg to 500 mg per day, 100 to 450 mg per day, 200 to 400 mg per day, 300 to 500 mg per day 350 to 500 mg per day, or 400 to 500 mg per day. In another aspect, the method further comprises a pharmaceutical agent, that can be a chemotherapeutic agent, that comprises one or more of paclitaxel, docetaxel, 5-fluorouracil, irinotecan, leucovorin calcium, oxaliplatin, capecitabine, interferon alpha, temozolomide, carboplatin, pegylated liposomal doxorubicin, topotecan, cisplatin, pemetrexed or a combination thereof. In another aspect, the VEGF/VEGFR inhibitor that is not axitinib or AG-013736 comprises ramicurimab, bevacuzamab, ranizumab, aflibercept, HLX12, or ziv-aflibercept. In another aspect, the VEGF/VEGFR inhibitor that is not axitinib therapeutically effective amount is from about 250 mg to 1,425 mg every two to three weeks, 400 mg to 2,600 mg every two to three weeks, 40 mg to 475 mg every two weeks. In another aspect, the therapeutically effective amount of the VEGF/VEGFR inhibitor that is not axitinib is administered at least one of continuously, intermittently, systemically, or locally. In another aspect, the therapeutically effective amount of the VEGF/VEGFR inhibitor that is not axitinib is administered orally, intravenously, subcutaneously, or intraperitoneally. In another aspect, the therapeutically or prophylactically effective amount of at least one of crenolanib, the pharmaceutical agent, and VEGF/VEGFR inhibitor that is not axitinib is administered to keep the subject in a state of stable disease or to cause a partial response, or complete response for as long as the subject needs such for the proliferative disease. In another aspect, the therapeutically effective amount of crenolanib is administered at least one of continuously, intermittently, systemically, or locally. In another aspect, the therapeutically effective amount of crenolanib is administered orally, intravenously, or intraperitoneally, and administered up to three times a day for as long as the subject is in need for the treatment of the proliferative disease. In another aspect, the crenolanib is crenolanib besylate, crenolanib phosphate, crenolanib lactate, crenolanib hydrochloride, crenolanib citrate, crenolanib acetate, crenolanib toluenesulphonate, or crenolanib succinate. In another aspect, the therapeutically effective amount of the pharmaceutical agent is administered at least one of continuously, intermittently, systemically, or locally. In another aspect, the therapeutically effective amount of the pharmaceutical agent is administered orally, intravenously, subcutaneously, or intraperitoneally. In another aspect, the cancer is not non-small cell lung cancer, small cell lung cancer, prostate, esophageal carcinoma, Ewing's sarcoma, or colorectal cancer. In another aspect, the dual inhibition of angiogenesis by inhibition of both PDGFR and VEGFR signaling is synergistic. In another aspect, the proliferative disorder is resistant to FOLFOX chemotherapy. In another aspect, the composition has reduced side-effects when compared to a composition that includes axitinib.

In another embodiment, the present invention includes a pharmaceutical composition for the treatment of cancer in a human subject comprising: crenolanib or salt thereof, a VEGF/VEGFR inhibitor that is not axitinib in a therapeutically effective amount for the treatment of the cancer. In another aspect, the cancer is at least one of: biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, uterine cancer, or other solid tumors. In another aspect, the therapeutically effective amount of crenolanib is from about 50 mg to 500 mg per day, 100 to 450 mg per day, 200 to 400 mg per day, 300 to 500 mg per day 350 to 500 mg per day, or 400 to 500 mg per day. In another aspect, the therapeutically effective amount of crenolanib is administered at least one of continuously, intermittently, systemically, or locally. In another aspect, the therapeutically effective amount of crenolanib is administered orally, intravenously, or intraperitoneally, and administered up to three times a day for as long as the subject is in need for the treatment of the proliferative disease. In another aspect, the crenolanib is crenolanib besylate, crenolanib phosphate, crenolanib lactate, crenolanib hydrochloride, crenolanib citrate, crenolanib acetate, crenolanib toluenesulphonate, and crenolanib succinate. In another aspect, the composition further comprises a chemotherapeutic agent selected from at least one of: one or more alkylating agents, one or more antimetabolites, or a combination thereof. In another aspect, the chemotherapeutic agent is an alkylating agent that comprises one or more of carmustine, chlorambucil, cyclophosphamide, ifosfamide, lomustine, streptozotocin, temozolomide, cisplatin, carboplatin, nedaplatin, or oxaliplatin. In another aspect, the alkylating agent therapeutically effective amount is from about 22 mg to 40 mg every 6 weeks, 150 to 200 mg every 6 weeks, 4 to 20 mg per day for 3 to 6 weeks, 2,000 to 4,750 given over 5 days, 4 to 19 mg per day, 1.44 to 3.12 g per day for 5 days in 3 weeks, 150 to 340 mg every 6 weeks, 600 to 1,300 mg per day for 5 days within 6 weeks, 90 to 390 mg daily, 24 to 260 mg per day for 5 days within 6 weeks, 240 to 1,690 mg every 6 weeks, 72 to 234 mg every 4 weeks 78 to 221 mg every 2 weeks. In another aspect, the chemotherapeutic agent is an antimetabolite that comprises one or more of methotrexate, pemetrexed, ralitrexed, fluorouracil, floxuridine, capcitabine, or gemcitabine. In another aspect, the antimetabolite therapeutically effective amount is from about 3.6 to 7.8 mg, 12 to 1,300 mg, 600 to 1,300 mg on day 1 of 21-day cycles. In another aspect, the chemotherapeutic agent is an anti-proliferative agent that comprises one or more of vinblastine, vinorelbine, vincristine, vindesine, vinflunine, paclitaxel, docetaxel, cabazitaxel, etoposide, teniposide, topotecan, irinotecan, doxorubicin, eiprubicin, valrubicin, mitoxantrone, bleomycin, estramustine, or mitomycin. In another aspect, the therapeutically effective amount of the chemotherapeutic agent is from about 0.48 mg to 3.7 mg, 7.2 mg to 28.9 mg, 30 mg to 78 mg, 96 mg to 455 mg, 72 mg to 260 mg, 400 mg to 760 mg every three weeks; 42 to 260 mg given days 1, 3, 5 of 21 day cycle, 198 mg to 650 mg once weekly, 0.9 mg to 3.9 mg daily for 5 days of 21 day cycle, 150 mg to 910 mg daily for 5 days of 21 day cycle, 48 mg to 195 mg every 21 days, 90 mg to 312 mg once every 3 or 4 weeks, 800 mg once weekly every 6 weeks, 14.4 mg to 36.4 mg every 21 days, 12.5 units to 47.5 units every 1 to 2 weeks, 500 mg to 1,520 mg per day, 12 mg to 52 mg every 6 to 8 weeks. In another aspect, the VEGF/VEGFR inhibitor that is not axitinib comprises ramicurimab, bevacuzamab, ranizumab, aflibercept, HLX12, ziv-aflibercept, vanucizumab, TX16, UB-922, BEVZ92, BCD-021, BI695502, CHS-5217, JHL1149, FKB238, Abevmy, ONS1045, PF06439535, HD204, SB8, TAB008, RPH001, BP102, HLX04, CT-P16, IBI305, LY01008, Mvasi, apagin, ranibizumab, CHS-3351, PF582, Xlucane, FYB201, razumab, CHS-2020, FYB203, ABP-201, sevacizumab, brolucizumab, CSL346, faricimab, hPV19, TAB014, UB-924, VGX-100, VX70, STI-A0168, CVX-241, BI 836880, ABT-165, conbercept, MP0250, MP0260, angiocal, abicipar pegol, anlotinib, apatinib, altiratinib, vandetanib, linifanib, motesanib, necuparanib, HLX12, APX004, CDP791, HLX-06, IBI302, icrucumab, IMC-1C11, IMC-3C5, MSB0254, navicixizumab, tanibirumab, V-DOS47, cabozantib, brivanib, dovitinib lactate, famitinib, foretinib, fruquintinib, golvatinib, henatinib, ponatinib, lenvatinib, lucitanib, sorafenib, nintedanib, orantinib, pegdinetanib, cediranib, rivoceranib, midostaurin, sitravatinib, regorafenib, sunitinib, sulfatnib, tesevatinib, tivozanib, valatanib, or pazopanib. In another aspect, the therapeutically effective amount of the VEGF/VEGFR inhibitor that is not axitinib is from about 250 mg to 1,425 mg every two to three weeks, 400 mg to 2,600 mg every two to three weeks, 40 mg to 475 mg every two weeks.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
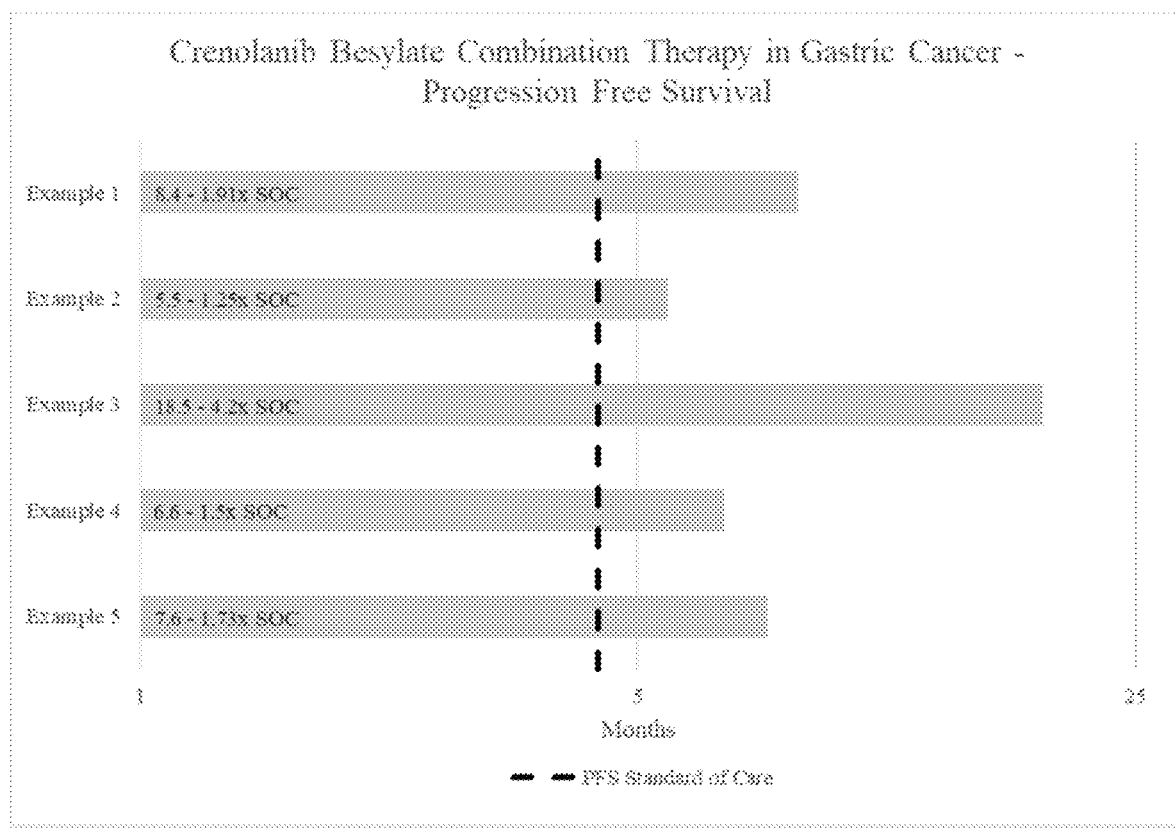
FIG. 1 shows the impact of the present invention on the progression free survival (PFS) of patients with gastroesophageal cancer. The clinical course for each patient is detailed in the "Example". Each patient was administered crenolanib besylate at a therapeutically effective concentration in combination with a VEGF signaling pathway inhibitor and a chemotherapeutic agent as second-line treatment. The length of time, in months, to disease progression was recorded. The median PFS for the standard of care for second-line gastric cancer (ramucirumab plus paclitaxel) is indicated by the dashed line (4.4 months). The PFS in months and fold-change improvement over standard of care for each patient is indicated. One patient, Example 3, remains on study as of December 2019.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

Definitions

As used herein, the term "subject" refers to an animal, such as a mammal or a human, who has been the object of treatment, observation or experiment.

As used herein, the term "therapeutically effective amount", refers to an amount of crenolanib or a pharmaceutical salt thereof, an anti VEGF/VEGFR inhibitor that is not axitinib, and/or a pharmaceutical agent, e.g., a chemotherapeutic agent, that in combination elicits the biological or medicinal response in a subject that is being sought by a researcher, veterinarian, medical doctor, or other clinician, which includes alleviation of the symptoms of the disease or disorder being treated. Methods for determining therapeutically effective doses for pharmaceutical compositions comprising a compound of the present invention are known in the art. Techniques and compositions for making useful dosage forms using the present invention are described in many references, including: P. O. Anderson, J. E. Knoben, and W. G. Troutman, Handbook of clinical drug data, 10th ed. New York; Toronto: McGraw-Hill Medical Pub. Division, 2002, pp. xvii, 1148 p; A. Goldstein, W. B. Pratt, and P. Taylor, Principles of drug action: the basis of pharmacology, 3rd ed. New York: Churchill Livingstone, 1990, pp. xiii, 836 p.; B. G. Katzung, Basic & clinical pharmacology, 9th ed. (Lange medical book). New York: Lange Medical Books/McGraw Hill, 2004, pp. xiv, 1202 p.; L. S. Goodman, J. G. Hardman, L. E. Limbird, and A. G. Gilman, Goodman and Gilman's the pharmacological basis of therapeutics, 10th ed. New York: McGraw-Hill, 2001, pp. xxvii, 2148 p.; J. P. Remington and A. R. Gennaro, Remington: the science and practice of pharmacy, 20th ed. Baltimore, Md.: Lippincott Williams & Wilkins, 2000, pp. xv, 2077 p.; W. Martindale, J. E. F. Reynolds, and Royal Pharmaceutical Society of Great Britain. Council, The extra pharmacopoeia, 31st ed. London: Royal Pharmaceutical Society, 1996, pp. xxi, 2739 p.; and G. M. Wilkes, Oncology Nursing Drug Handbook 2016, 20 ed. Sudbury: Jones & Bartlett Publishers, 2016, p. 1500 p., relevant portions of each are incorporated herein by reference. As used herein, the phrase "in combination with" refers to the administration of crenolanib or a pharmaceutically acceptable salt thereof, an anti-VEGFR/VEGF inhibitor that is not axitinib, and in some instances a chemotherapeutic agent either simultaneously or sequentially in any order, such as, for example, at repeated intervals as during a standard course of treatment for a single cycle or more than one cycle, such that one agent can be administered prior to, at the same time, or subsequent to the administration of the other agents, or any combination thereof. In one example, the composition includes crenolanib or a pharmaceutically acceptable salt thereof, ramicurimab, and paclitaxel in amounts sufficient for the treatment of a disease.

As used herein, the term "composition" refers to a product comprising the specified ingredients in the specified amounts, as well as any product that results, directly or indirectly, from combinations of the specified ingredients in the specified amounts.

As used herein, the term "antibody" is used in the broadest sense and includes various antibody structures, including but not limited to monoclonal antibodies, polyclonal antibodies, multispecific antibodies (i.e., bispecific antibodies), and antibody fragments as long as they still exhibit desired antigen-binding ability.

As used herein, the terms "proliferative disorder(s)" and "cell proliferative disorder(s)" refer to excess cell proliferation of one or more subset of cells in a multicellular organism resulting in harm (i.e. discomfort or decreased life expectancy) to the multicellular organism. Cell proliferative disorders can occur in different types of animals and humans. As used herein, "cell proliferative disorders" include neoplastic disorders.

As used herein, the term "neoplastic disorder" refers to a tumor resulting from abnormal or uncontrolled cellular growth. Examples of neoplastic disorders include, but are not limited to the following disorders, for instance: cancers such as carcinoma, lymphoma, blastoma, sarcoma, and leukemias. Non-limiting examples of proliferative disorders for treatment with the present invention include biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, uterine cancer, or other solid tumors. In certain embodiments, the present invention is directed at the use of a pharmaceutical composition comprising a pharmaceutical agent, VEGF/VEGFR inhibitor that is not axitinib, and crenolanib or a pharmaceutically acceptable salt thereof in an amount sufficient for the treatment of a neoplastic disorder, e.g., gastric cancer.

As used herein, the term "pharmaceutical agent" is used herein to refer to one or more active agents that may be used in conjunction with the composition of crenolanib (or salts thereof) and a VEGF/VEGFR antagonist that are not antimitotic or anti-proliferative per se, but that may be used in conjunction to activate the immune system to target proliferative diseases or disorders, such as, e.g., cytokines, lymphokines, and the like.

As used herein, the term "chemotherapeutic agent" refers to anti-cell proliferation therapies such as alkylating agents, antimetabolites, and natural products. Chemotherapy is known to those skilled in the art and the appropriate dosage(s) and scheme(s) for chemotherapy will be similar to those already employed in clinical therapies wherein the chemotherapy is delivered in combination with other therapies or used alone. A variety of chemotherapeutic agents may be used in combination with the present invention. By way of example only, taxane compounds (such as docetaxel), are safely administered in combination in the compound of the present invention in a dosage of 75 mg per square meter (mg/m$^2$) of body surface area. The skilled artisan will recognize that the selected chemotherapeutic will have a dosage based on a variety of factors, such as the weight, age, gender, extent of disease, etc., that will change the dosage within best medical practice for the intended treatment.

As used herein, the term "alkylating agent" refers to a group of chemotherapies that classically have caused the addition of an alkyl group to DNA but is now used to refer to any chemotherapy that causes addition of a small chemical moiety to DNA. Examples of alkylating agents include, but are not limited to carmustine, chlorambucil, cyclophosphamide, ifosfamide, lomustine, streptozotocin, temozolomide, cisplatin, carboplatin, nedaplatin, oxaliplatin.

As used herein, the term "antimetabolite" refers to a group of chemotherapies that structurally similar to a naturally occurring chemical in the body that it can take the place of said chemical in binding to an enzyme or protein but are different enough that they prohibit the termination of the normal action of the chemical in the body. Examples of antimetabolites include, but are not limited to methotrexate, pemetrexed, ralititrexed, fluorouracil, floxuridine, capcitabine, gemcitabine.

As used herein, the term "natural products" refers to a group of chemotherapeutic agents and/or chemotherapies that are purified organic compounds originally isolated from a living organism that are produced by pathways of secondary metabolism. Examples of natural products includes but is not limited to vinblastine, vinorelbine, vincristine, vindesine, vinflunine, paclitaxel, docetaxel, cabazitaxel, etoposide, teniposide, topotecan, irinotecan, doxorubicin, eiprubicin, valrubicin, mitoxantrone, bleomycin, estramustine, mitomycin.

Unfortunately, the use of axitinib (a small molecule tyrosine kinase inhibitor) to target VEGFR, has significant side effects, including: thromboembolic (both venous and arterial) events; hemorrhagic events (including cerebral hemorrhage), hypertension, gastrointestinal perforations and fistula, changes in thyroid function, clotting factor inhibition, proteinuria, elevated liver enzymes (AST, ALT and bilirubin), and loss of hepatic function, leading to the need to decrease dosing, and thus, effectiveness, leading to an end of the study and the failure to increase dosing.

Combinatorial approach to full inhibition of angiogenesis by block both VEGFR and PDGFR signaling.

The present invention comprises the combination of a general pharmaceutical agent, a VEGF/VEGFR antibody, and crenolanib (4-Piperidinamine, 1-[2-[5-[(3-methyl-3-oxetanyl) methoxy]-1H-benzimidazol-1-yl]-8-quinolinyl]) and its pharmaceutically acceptable salts, as a method for reducing or inhibiting tumor growth while simultaneously inhibition angiogenesis by blocking both endothelial cells (by blocking VEGFR signaling) and pericytes (by blocking PDGFRB signaling) in a subject. Examples of VEGF/VEGFR inhibitors include those that block the activation of VEGFR by binding to VEGF, affect the expression of VEGF or VEGFR, affect downstream signaling from VEGFR, and the like. Examples of VEGF/VEGFR inhibitors that are not axitinib comprise: ramicurimab, bevacuzamab, ranizumab, aflibercept, HLX12, ziv-aflibercept, vanucizumab, TX16, UB-922, BEVZ92, BCD-021, BI695502, CHS-5217, JHL1149, FKB238, Abevmy, ONS1045, PF06439535, HD204, SB8, TAB008, RPH001, BP102, HLX04, CT-P16, IBI305, LY01008, Mvasi, apagin, ranibizumab, CHS-3351, PF582, Xlucane, FYB201, razumab, CHS-2020, FYB203, ABP-201, sevacizumab, brolucizumab, CSL346, faricimab, hPV19, TAB014, UB-924, VGX-100, VX70, STI-A0168, CVX-241, BI 836880, ABT-165, conbercept, MP0250, MP0260, angiocal, abicipar pegol, anlotinib, apatinib, altiratinib, vandetanib, linifanib, motesanib, necuparanib, HLX12, APX004, CDP791, HLX-06, IBI302, icrucumab, IMC-1C11, IMC-3C5, MSB0254, navicixizumab, tanibirumab, V-DOS47, cabozantib, brivanib, dovitinib lactate, famitinib, foretinib, fruquintinib, golvatinib, henatinib, ponatinib, lenvatinib, lucitanib, sorafenib, nintedanib, orantinib, pegdinetanib, cediranib, rivoceranib, midostaurin, sitravatinib, regorafenib, sunitinib, sulfatnib, tesevatinib, tivozanib, valatanib, or pazopanib.

Crenolanib has the formula:

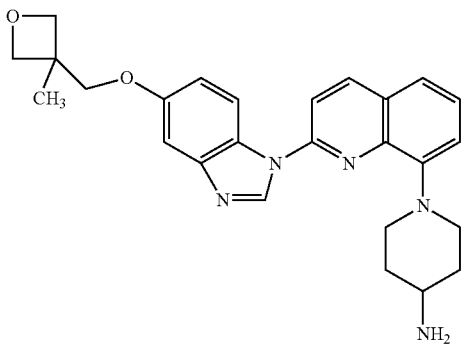 [SMILES: CC1(COc2ccc3c(c2)ncn3-c2ccc3cccc(N4CCC(N)CC4)c3n2)COC1]

Crenolanib can exist in a variety of salt forms, including but not limited to: Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate, but may also be made available free of salts. Preparation of the compounds of the present invention. General synthetic methods for preparing the compounds of Formula I are provided in, e.g., U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application Publication No. US 2005/0124599 (Pfizer, Inc.) and U.S. Pat. No. 7,183,414 (Pfizer, Inc.), relevant portions incorporated herein by reference.

By way of example, Crenolanib besylate is an orally bioavailable, selective, and potent type I TKI of class III receptor tyrosine kinases (RTKs). The chemical name of crenolanib besylate is 4-piperidinamine, 1-[2-[5-[(3-methyl-3-oxetanyl) methoxy]-1H-benzimidazol-1-yl]-8-quinolinyl]-, monobenzenesulfonate. The compound has the ability to inhibit PDGFR-α and PDGFR-β. Crenolanib does not inhibit any other known RTKs (e.g., VEGFR or fibroblast growth factor receptor) or serine/threonine kinases (e.g., Abl, Raf) at concentrations that are used clinically.

Angiogenesis is a complex biological process that requires a variety of factors and signaling pathways to stimulate the migration and proliferation of the component cell types, and to establish functional blood vessels. Angiogenesis is driven by pro-angiogenic factors like vascular endothelial growth factor (VEGF) that forms new capillary networks. PDGF activation of PDGFR-β is responsible for the migration of supporting pericytes to support and stabilize angiogenesis [2, 3]. Inhibitors of VEGF, such as Avastin (bevacizumab), have been approved in multiple different types of cancer, including colorectal, non-small cell lung, ovarian, cervical, renal cell carcinoma, and glioblastoma (GBM). Bevacizumab only has single agent activity in ovarian cancer (trials). Bevacizumab in combination with chemotherapy has seen improvements in PFS in metastatic 1st line breast cancer, metastatic 1st and 2nd line colorectal cancer, metastatic 1st line NSCLC, metastatic 1st and 2nd line ovarian cancer, metastatic 1st line prostate cancer, and metastatic 1st line renal cancer [4-17]. Ramucirumab is an antibody against VEGF receptor 2 (VEGFR2), was evaluated in two different phase III clinical trials (RAINBOW and REGARD), which led to its approval alone or in combination with paclitaxel in gastric cancer, non-small cell lung cancer, and colorectal cancer. Another antibody against VEGF, aflibercept, also blocks VEGF binding to its receptor and is approved for use in wet macular degeneration and metastatic colorectal cancer. These VEGF inhibitors have provided crucial evidence highlighting the role and significance of targeting angiogenesis across multiple solid tumors [18-20]. Ramucirumab has also been evaluated in the treatment of colorectal cancer and non-small cell lung carcinoma. In a Phase III study of ramucirumab in combination with chemotherapy in metastatic colorectal cancer (RAISE), patients treated with ramucirumab and chemotherapy had modestly increased overall survival (OS; 13.3 versus 11.7 months) and progression-free survival (PFS; 5.7 versus 4.5 months) over patients treated with placebo and chemotherapy. The improved results seen in this trial supported the granting of marketing authorization for ramucirumab in metastatic colorectal cancer [21]. Ramucirumab has also been granted marketing approval in the setting of non-small cell lung cancer (NSCLC). In a Phase III clinical trial evaluating the efficacy of ramucirumab in combination with docetaxel versus placebo with docetaxel (REVEL), patients treated with ramucirumab had increased OS (11.2 versus 9.8 months) [22]. As with the results of the RAINBOW study, virtually all patients in both the RAISE and REVEL trials eventually developed disease progression. These modest results demonstrate the existence of underlying and acquired mechanisms of resistance to VEGF-pathway inhibition.

Despite the incremental benefit of a VEGF/VEGFR antibody and chemotherapy, 13% of patients in the RAINBOW study experienced progressive disease (PD) as their best response and virtually all patients eventually developed progression. In addition, ramucirumab monotherapy is associated with a response rate (RR) of only 3% and a progression-free survival (PFS) improvement of only 0.8 months over placebo.

The susceptibility of established tumor blood vessels to interference with VEGF/VEGFR-2 signaling may be restricted to a fraction of immature vessels that lack co-localization with pericytes [3]. Pericytes are believed to be either generated by in situ differentiation from mesenchymal cells or by migration and de-differentiation of arterial smooth muscle cells. Contact between endothelial cells and peri-endothelial support cells such as pericytes stabilizes new blood vessels and promotes endothelial survival. Blood vessels in many experimental and human tumor types are closely associated with pericytes, allowing these tumors to survive targeting the VEGF pathway alone. Additional targeting of pericyte recruitment and pericyte/endothelial cell interaction may enhance tumor vessel destruction after interference with VEGF/VEGFR-2 signaling. The PDGF/PDGFR pathway has been implicated in the maintenance of interstitial pressure.

One of the postulated mechanisms of resistance to anti-VEGF therapy is upregulation of signaling through the PDGF/PDGFR pathway. The platelet-derived growth factors (PDGF-A, PDGF-B, PDGF-C, and PDGF-D) or ligands in their monomeric form are inactive and linked by amino acid disulfide bonds to form active one homodimeric and four heterodimeric isoforms: PDGF-AA, PDGF-BB, PDGF-CC, PDGF-DD, and PDGF-AB. These isoforms exert their biological effects on either homodimeric PDGFR-αα or PDGFR-ββ or heterodimeric PDGFR-αβ receptors through specific binding, resulting in their activation. Oncogenic alteration of PDGFR and overexpression of PDGF ligands and receptors contributes to tumorigenesis. Cancers in which PDGFR is altered include pancreatic, ovarian, breast, gastric, thymoma, gastrointestinal stromal tumor, osteosarcoma, and hepatocellular carcinoma. For example, data over the last decade has provided strong clinical and pre-clinical significance of the role of anti-angiogenesis in gastric cancer and critical role played by PDGFR-β in angiogenesis. There is also evidence that shows high PDGF-D expression is strongly associated with tumor progression, recurrence, distant metastasis, and poor outcomes in patients with gastric cancer, further highlighting the crucial role PDGF and PDGFR play in cancer and the urgent need to target this pathway [23].

In a mouse model, Erber et al., demonstrated that treatment of implanted tumors with an anti-VEGFR TKI, SU5416, failed to induce regression of established blood vessels, although it suppressed further neovascularization and, therefore, prevented tumor growth [24]. The underlying mechanism of resistance arose from the recruitment of pericytes to stabilize the tumor blood vessels. PDGFR-β expression by pericytes and endothelial cells also doubled. Subsequently, they demonstrated that dual inhibition with a TKI with activity against both VEGFR and PDGFR, SU6668, resulted in regression of established tumor vessels, leading to an increase in microvascular permeability and microvascular hemorrhage. This led to decreased oxygenation in the tumor tissue, endothelial cell apoptosis and suppression of tumor growth. Although PDGFR-β expression was elevated and comparable to the SU5416-treated tumors, the association of pericytes with endothelial cells was less intimate than in the SU5416-treated tumors, suggesting that PDGFR inhibition may exert its effects at this level [24].

PDGFR inhibitors known in the art include but are not limited to avapritinib (also known as Blu-285, Blueprint Medicines Corp.); CBT-102 (CBT Pharmaceuticals); dovitinib lactate (also known as CHIR-258, Oncology Venture A/S); Gleevec (also known as Glivec, imatinib, Novartis AG); E7050 (also known as golvatinib, Eisai, Co., Ltd.); Latruvo (also known as olaratumab, Eli Lily & Co.); Lenvima (also known as lenvatinib, E7080, Eisai, Co., Ltd.); Lucitanib (also known as AL3810, Clovis Oncology, Inc.); macitinib (also known as AB1010, AB Science A. B.); Nexavar (also known as sorafenib, Amgen, Inc.); Ofev (also known as nintedanib, BIBF-1120, Boehringer Ingelheim GmbH); PDGF-BB (Adocia SAS); Regranex (also known as becalpermin, Novartis AG); Stivarga (also known as regorafenib, Bayer AG); Sutent (also known as sunitinib, Pfizer, Inc.); Tasigna (also known as nilotinib, AMN107, Novartis AG); telatinib (also known as BAY 57-9352, Eddingpharm); Votrient (also known as pazopanib, Novartis AG); X-82 (Xcovery, Inc.).

These PDGFR inhibitors have either been or are currently being investigated in the preclinical setting, phase I, phase II, or phase III trials as monotherapy or combination studies in relapsed or refractory tumors. In most patients, the clinical response is short-lived, and patients experience adverse side effects. End study response criteria for patients treated with PDGFR inhibitor includes a partial tumor response and an increase in delay time to progression. To effectively treat treatment-resistant cancers, especially those that are resistant to anti-angiogenesis agents, and overcome the significant unmet need in this patient population, an inhibitor that significantly abrogates PDGF/PDGFR signaling can help decrease relapse rates and increase overall survival in early stage disease patients. The current invention seeks to overcome disadvantages of the prior art.

Tumor interstitial pressure. An additional mechanism of chemotherapy resistance that has been postulated is the high interstitial pressure within tumors, which results in a lower hydrostatic gradient from the vasculature to the interstitium and reduced passage of solutes, including chemotherapy drugs, across the capillary membrane into the tumor [25].

It has previously been hypothesized that anti-angiogenic drugs such as bevacizumab, an antibody against VEGF-A, may function in part by normalizing the tumor vasculature, reducing the tumor interstitial pressure and thereby increase chemotherapy delivery into the tumor. This function is somewhat related but distinct from the proposed role of anti-angiogenic therapy in inhibiting neovascularization and would explain the lack of single-agent activity of bevacizumab—and ramucirumab.

The PDGF-PDGFR pathway has been implicated in the maintenance of interstitial pressure and there are also data that anti-PDGFR therapies can reduce interstitial pressures. Imatinib, which has activity against the PDFGR-β tyrosine kinase, has been shown in a rat model to decrease interstitial hypertension and to increase the capillary-to-interstitium transport of solutes [26]. In another series of experiments by the same group, treatment with imatinib resulted in increased anti-tumor effect of paclitaxel and increased paclitaxel uptake by the tumors [27].

The present invention is based on the novel observation that a combination of inhibition of PDGF and VEGF/VEGFR (with an inhibitor that is not axitinib) and chemotherapeutic agents significantly improves outcomes for patients with cancer.

The present inventors recognize for the first time synergy between PDGF and VEGF inhibition. As such, there is a rationale and basis to combining PDGF and VEGF pathway inhibitors with cytotoxic chemotherapy but to also strongly consider alternative agents.

In summary, crenolanib is generally well tolerated as a single agent and when combined with chemotherapy; the most common adverse events are gastrointestinal toxicities, elevations in liver enzymes and bilirubin, and edema/effusions. Unlike axitinib, VEGF/VEGFR antibodies are associated with minimal toxicity and the combination of these antibodies and chemotherapy is very well-tolerated [4-19, 21, 22, 28-32]. In particular, axinitinib monotherapy (in renal cancer patients) is associated with notable toxicities, including all-grade fatigue, anorexia, nausea, diarrhea and hand-foot syndrome in >25% of patients[33]. Additionally, paclitaxel is less myelosuppressive than docetaxel. These improved toxicities support the combination of crenolanib and an alternative VEGFR inhibitor (including ramucirumab) in addition to and chemotherapy in patients with advanced cancers.

In one embodiment to this aspect, the present invention provides a method for reducing or debulking the tumor while simultaneously inhibiting angiogenesis by blocking not only VEGF signaling which inhibits the growth and migration of endothelial cells, but also by blocking PDGF signaling which inhibits the growth and migration of pericytes which stabilize newly formed or forming blood vessels in a subject comprising the step of administering the compounds of the present invention to the subject, wherein the combination is provided at least one of sequentially or simultaneously.

In other embodiments, the present invention provides therapeutic methods for treating a subject with a cell proliferative disorder driven by abnormal new vasculature formation. In one example, the invention provides methods for treating a cell proliferative disorder that is dependent on recruitment and growth of new vasculature to support tumor growth, comprising administration of a therapeutically effective amount of a pharmaceutical composition comprising the compounds of the present invention in a subject.

Administration of the therapeutic agents can occur upon manifestation of symptoms characteristic of the cell proliferative disorder, such that a disease or disorder is treated.

The present disclosure discloses a method for treating a subject with a cell proliferative disorder that is dependent on recruitment of new blood vasculature for the sustainment and growth of said proliferative disorder. In one example, the invention provides methods for treating a proliferative disorder comprising administration of a therapeutically effective amount of a pharmaceutical composition comprising a pharmaceutical agent, VEGF/VEGFR inhibitor that is not axitinib, and crenolanib in a subject. Administration of the present invention can occur upon manifestation of symptoms characteristic of a solid tumor cell proliferative disorder, such that a disease or disorder treated.

A main advantage of the combination treatments of the invention is the ability of producing marked anti-tumor effects in a patient without causing significant toxicities or adverse events, so that the patient benefits from the combination treatment method overall. The efficacy of the combination treatment of the invention can be measured by many endpoints commonly used to evaluate cancer treatments, including but not limited to, tumor regression, tumor size shrinkage, time to progression, overall survival, and quality of life. Because the invention related to the use of a combination of unique anti-tumor agents, novel approaches for determining efficacy or any particular part of the combination therapy of the present invention can be employed, including for example, measurement of biomarkers of VEGF and/or PDGF signaling, such as VEGF-AB, or PDGF, and measurement of response through radiological imaging.

In one embodiment of the present invention, the chemotherapeutic agent, anti-VEGF/VEGFR inhibitor that is not axitinib, and crenolanib or a pharmaceutically acceptable salt thereof may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art and will vary with the compound of the present invention used, the mode of administration, the time of administration, the strength of the preparation, and the details of the disease condition. Factors associated with patient characteristics, such as age, weight, and diet will call for dosage adjustments.

Preparation of the compounds of the present invention. General synthetic methods, which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

Example 1

Effect of crenolanib besylate combination therapy in a gastroesophageal junction (GEJ) adenocarcinoma patient with metastases in the liver: Partial Response per RECIST 1.1 criteria.

A 53-year-old male was initially diagnosed September 2017 with esophageal cancer. The patient was treated with palliative FOLFOX chemotherapy: a combination of a fluoropyrimidine (fluorouracil, or 5-FU), a platinum compound (oxaliplatin), and leucovorin. Palliative chemotherapy began late September 2017 and continued until January 2018. Oral capecitabine was then given to the patient for 5 months until the patient's cancer progressed June 2018 when a CT scan revealed that the patient had progressive disease and the cancer had metastasized to the liver, upper stomach, and lymph nodes.

In response to progression on first-line therapy, the patient was provided oral crenolanib besylate (PDGFRβ inhibitor) in combination with paclitaxel and ramucirumab (VEGFR2 inhibitor) on a clinical trial for second-line advanced esophagogastric adenocarcinoma (NCT03193918). At baseline, the patient had a sum of diameters of 112 mm, per RECIST 1.1 criteria. After 8 weeks on combination treatment, the patient achieved stable disease (SD) per RECIST 1.1 criteria with a decrease in sum of diameters to 76 mm. After 16 weeks on treatment, the patient achieved a partial response (PR) per RECIST 1.1 criteria with a 40% decrease in sum of diameters from baseline. After an additional 8 weeks on treatment, the patient achieved a total decrease of 57% in sum of diameters from baseline. On crenolanib therapy, this patient had a progression-free survival (PFS) of 7.8 months. This is a significant improvement over the PFS of 4.4 months observed with paclitaxel plus ramucirumab, which is the standard of care in second-line gastric cancer at the time of filing. [19]

Example 2

Effect of crenolanib besylate combination therapy in a stage IIIB, gastric adenocarcinoma patient with metastatic disease to lymph nodes: Partial Response per RECIST 1.1 criteria.

A 68-year-old female was diagnosed September 2015 with stage IIIB metastatic cancer in the stomach and lymph nodes. She underwent a partial gastrectomy and started adjuvant FOLFOX chemotherapy October 2015. She remained on the FOLFOX regimen for 12 cycles until April 2016. Despite adjuvant chemotherapy treatment, a CAT scan October 2016 showed increased metastatic disease in the lymph node, which prompted palliative chemotherapy with fluorouracil. The patient continued to progress and was found to have metastatic disease to the gastrohepatic ligament, lungs, and lymph nodes in October 2017.

In response to progression on first-line therapy, the patient was provided oral crenolanib besylate (PDGFRβ inhibitor) in combination with paclitaxel and ramucirumab (VEGFR2 inhibitor) on a clinical trial for second-line advanced esophagogastric adenocarcinoma (NCT03193918). At baseline, the patient had a sum of diameters of 35 mm, per RECIST 1.1 criteria. After only 8 weeks on combination treatment, the patient achieved a PR per RECIST 1.1 criteria with a decrease in sum of diameters to 21 mm. The patient maintained a PR in follow-up CT assessments and remained on crenolanib besylate, ramucirumab, and paclitaxel combination treatment for 22 weeks. The patient achieved a 5.5-month PFS while on crenolanib besylate combination treatment, an improvement over current standard of care in second-line gastric cancer.

Example 3

Effect of crenolanib besylate combination therapy in a stage IV, invasive gastric adenocarcinoma patient: Stable Disease per RECIST 1.1 criteria.

A 50-year-old male was diagnosed with invasive gastric cancer in May 2016. The tumor was found to arise from *Helicobacter pylori* (*H. pylori*)-associated chronic gastritis. The patient was treated with neoadjuvant FOLFOX chemotherapy. After 12 cycles of FOLFOX chemotherapy, the patient underwent a partial gastrectomy and lymphadenectomy in November 2018. Despite 6 months of neoadjuvant chemotherapy and a surgical approach, a follow-up CT scan and laparoscopy in April 2018 revealed the cancer had metastasized to the ileum and peritoneum.

In response to progression on first-line therapy, the patient was provided oral crenolanib besylate (PDGFRβ inhibitor) in combination with paclitaxel and ramucirumab (VEGFR2 inhibitor) on a clinical trial for second-line advanced esophagogastric adenocarcinoma (NCT03193918). At baseline, the CT scan from May 2018 revealed a sum of diameters of 28 mm, per RECIST 1.1 criteria. After 80 weeks of crenolanib besylate combination therapy, the patient has maintained SD, per RECIST 1.1 criteria. As of early December 2019, the patient remains on trial with an approximate PFS of 18.5 months and is clinically stable. This patient's PFS is over four times longer than that observed with current standard of care and demonstrates the benefit and utility of the present invention.

Example 4

Effect of crenolanib besylate combination therapy in a metastatic esophageal adenocarcinoma with extensive mediastinal and upper abdominal lymph node metastases: Stable Disease per RECIST 1.1 criteria.

A 32-year-old male was initially diagnosed with metastatic cancer in the esophagus and lymph nodes in October 2016. He was started on FOLFOX chemotherapy, a combination of a fluoropyrimidine (fluorouracil, or 5-FU) and a platinum compound (oxaliplatin) and remained on FOLFOX for 3 months. The patient remained on a fluoropyrimidine until May 2017 and was given another platinum compound (cisplatin) for approximately 2 months from early April 2017 to the end of May 2017. Despite the combination of a fluoropyrimidine and 2 separate platinum compounds, the patient progressed June 2017 when a CT scan revealed increased disease in the lymph nodes and metastatic disease to stomach and liver.

In response to progression on first-line therapy, the patient was provided oral crenolanib besylate (PDGFRβ inhibitor) in combination with paclitaxel and ramucirumab (VEGFR2 inhibitor) on a clinical trial for second-line advanced esophagogastric adenocarcinoma (NCT03193918). At baseline, the CT scan from June 2017 revealed a sum of diameters of 49 mm, per RECIST 1.1 criteria. After 8 weeks on combination treatment, patient achieved SD, per RECIST 1.1, with a decrease in sum of diameters to 42 mm.

The patient achieved a PFS of 6.6 months while on crenolanib besylate combination treatment, which is a significant improvement over standard of care.

Example 5

Effect of crenolanib besylate in a metastatic gastric adenocarcinoma: Stable Disease per RECIST 1.1 criteria.

A 72-year-old male was initially diagnosed August 2015 with gastric adenocarcinoma. The patient was treated with surgery and neoadjuvant FOLFOX chemotherapy. After surgery, the patient received maintenance 5-fluorouracil until July 2018, when a CT scan revealed the patient had progressive disease and worsening peritoneal carcinomatosis.

In response to progression on first-line therapy, the patient was provided oral crenolanib besylate (PDGFRβ inhibitor) in combination with paclitaxel and ramucirumab (VEGFR2 inhibitor) on a clinical trial for second-line advanced esophagogastric adenocarcinoma (NCT03193918). At baseline, the patient had a sum of diameters of 68 mm, per RECIST 1.1 criteria. The patient maintained clinically stable disease for 28 weeks while on crenolanib treatment, per RECIST 1.1 criteria. The patient achieved a PFS of over 7 months on crenolanib besylate combination treatment, a significant improvement over the standard of care of ramucirumab plus paclitaxel.

Figure 2:
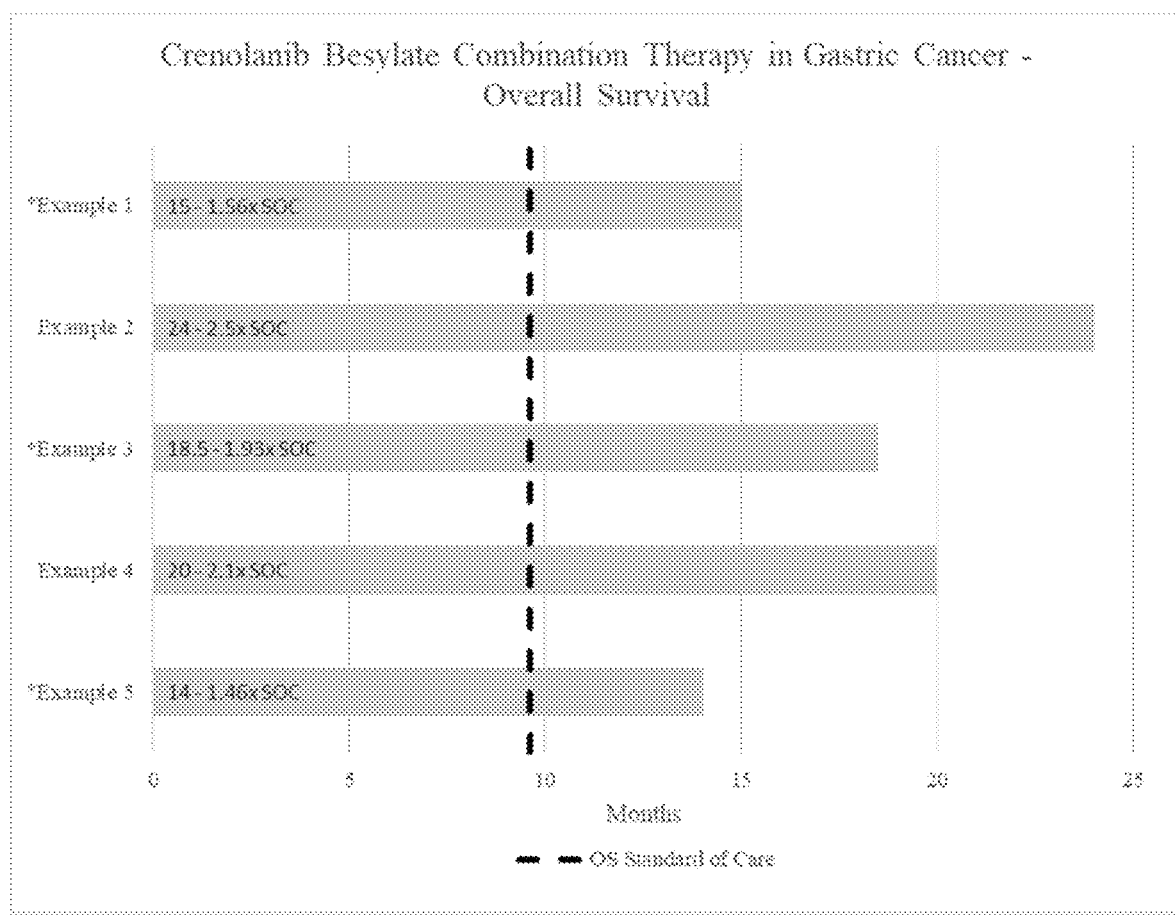
FIG. 2 shows the impact of the present invention on the overall survival (OS) of patients with gastroesophageal cancer. The clinical course for each patient is detailed in the "Example" section. Each patient was administered crenolanib besylate at a therapeutically effective concentration in combination with a VEGF signaling pathway inhibitor and a chemotherapeutic agent as second-line treatment. The length of time, in months, to death was recorded. The median OS for the standard of care for second-line gastric cancer (ramucirumab plus paclitaxel) is indicated by the dashed line (9.6 months). The OS in months and fold-change improvement over standard of care for each patient is indicated. Three patients, Example 1, Example 3, and Example 5 remain alive as of December 2019 (indicated by "*").

The basic information, including PFS and survival, for the above examples are displayed in Table 1 (examples of partial response to treatment) and Table 2 (examples of stable disease). For all examples, the PFS was significantly longer than that seen on paclitaxel plus ramucirumab, the standard of care treatment for second-line gastric cancer. This improvement in PFS can be readily seen in FIG. 1, which shows the PFS observed for each patient on crenolanib besylate combination therapy, as well as a reference (dashed line) of the median PFS observed with standard of care. In addition to significantly improved PFS, the present invention also extended the overall survival (OS) for these examples (FIG. 2). The median OS seen with paclitaxel plus ramucirumab treatment was 9.6 months.[19] The examples described herein all survived for 14 months or more, with three examples (1, 3, and 5) remaining alive as of December 2019 (indicated as a "+" in the survival column of Tables 1 and 2 and denoted with "*" in FIG. 2).

TABLE 1 shows the basic characteristics and clinical course of second-line gastroesophageal cancer patients treated with the present invention who achieved a Partial Response to crenolanib besylate combination therapy. Both patients achieved >40% shrinkage of their tumors, with Example 1 achieving 57% shrinkage. Also listed is the progression-free survival (PFS) and overall survival (OS) for each patient. Patient Example 1 remains alive as of December 2019, as indicated by the "+" in the survival column.

TABLE 1

Partial Response Summary Data from Gastroesophageal Cancer Patients
Treated with Crenolanib Besylate Combination Therapy
Examples - Partial Response to Crenolanib Combination Treatment

| Example | Age | Sex | Site of Primary Tumor | Previous Chemotherapy | Tumor Shrinkage | PFS (months) | Survival (months) |
|---|---|---|---|---|---|---|---|
| 1 | 53 | M | Esophageal | FOLFOX | 57% | 7.8 | 15+ |
| 2 | 68 | F | Gastric | FOLFOX | 40% | 5.5 | 24 |

TABLE 2 shows the basic characteristics and clinical course of second-line gastroesophageal cancer patients treated with the present invention who maintained Stable Disease while on crenolanib besylate combination therapy. All three patients remained clinically stable for at least 6 months, and one patient "Example 3" remains on-study, and is currently receiving crenolanib besylate combination treatment, as of December 2019. Also listed is the OS for each patient. Two patients, Example 3 and Example 5, remain alive as of December 2019, as indicated by the "+" in the survival column.

TABLE 2

Stable Disease Summary Data from Gastroesophageal Cancer Patients
Treated with Crenolanib Besylate Combination Therapy.
Examples - Stable Disease on Crenolanib Combination Treatment

| Example | Age | Sex | Site of Primary Tumor | Previous Chemotherapy | PFS (months) | Survival (months) |
|---|---|---|---|---|---|---|
| 3 | 50 | M | Gastric | FOLFOX | 18.5+ | On-study |
| 4 | 32 | M | Esophageal | FOLFOX | 6.6 | 20 |
| 5 | 72 | M | Gastric | FOLFOX | 7 | 14+ |

From the above examples, it is evident to those skilled in the art that the present invention is of significant benefit to patients showing statistically significant improvement outcomes as compared to standard of care. The additive benefit of crenolanib besylate is of an unexpectedly significant magnitude, especially when skilled artisans consider that the improvement of the addition of ramucirumab to paclitaxel resulted in only a 52% improvement in PFS and a 30% improvement in OS, compared to the median 72% improvement in PFS and 93% improvement in OS seen with the present invention.[19] In addition, there is not a significant expectation of success as responses to anti-angiogenic therapy of the prior art, including ramucirumab, are at best transient, with most patient progressing on treatment.[19] In fact, in general, the impact of anti-angiogenesis agents on survival, as taught in the prior art [34], has been disappointing. This history of, at best, modest and transient results of targeted angiogenesis agents, either as single agent therapy or in combination with chemotherapy, highlights the unexpected utility and benefit of the present invention.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

[1] M. Michael, G. Vlahovic, K. Khamly, K. J. Pierce, F. Guo, and A. J. Olszanski, "Phase Ib study of CP-868,596, a PDGFR inhibitor, combined with docetaxel with or without axitinib, a VEGFR inhibitor," Br J Cancer, vol. 103, no. 10, pp. 1554-61, Nov. 9, 2010.

[2] P. Lindahl, B. R. Johansson, P. Leveen, and C. Betsholtz, "Pericyte loss and microaneurysm formation in PDGF-B-deficient mice," Science, vol. 277, no. 5323, pp. 242-5, Jul. 11, 1997.

[3] L. E. Benjamin, D. Golijanin, A. Itin, D. Pode, and E. Keshet, "Selective ablation of immature blood vessels in established human tumors follows vascular endothelial growth factor withdrawal," J Clin Invest, vol. 103, no. 2, pp. 159-65, January 1999.

[4] C. Aghajanian et al., "OCEANS: a randomized, double-blind, placebo-controlled phase III trial of chemotherapy with or without bevacizumab in patients with platinum-sensitive recurrent epithelial ovarian, primary peritoneal, or fallopian tube cancer," J Clin Oncol, vol. 30, no. 17, pp. 2039-45, Jun. 10, 2012.

[5] A. M. Brufsky et al., "RIBBON-2: a randomized, double-blind, placebo-controlled, phase III trial evaluating the efficacy and safety of bevacizumab in combination with chemotherapy for second-line treatment of human epidermal growth factor receptor 2-negative metastatic breast cancer," J Clin Oncol, vol. 29, no. 32, pp. 4286-93, Nov. 10, 2011.

[6] A. Chan, D. W. Miles, and X. Pivot, "Bevacizumab in combination with taxanes for the first-line treatment of metastatic breast cancer," Ann Oncol, vol. 21, no. 12, pp. 2305-15, December 2010.

[7] F. C. Cananzi et al., "Chronic" metastatic pancreatic acinar cell carcinoma," Pancreatology, vol. 13, no. 5, pp. 549-52, September-October 2013.

[8] B. J. Giantonio et al., "Bevacizumab in combination with oxaliplatin, fluorouracil, and leucovorin (FOLFOX4) for previously treated metastatic colorectal cancer: results from the Eastern Cooperative Oncology Group Study E3200," J Clin Oncol, vol. 25, no. 12, pp. 1539-44, Apr. 20, 2007.

[9] K. Blackwell et al., "Circulating D-dimer levels are better predictors of overall survival and disease progression than carcinoembryonic antigen levels in patients with metastatic colorectal carcinoma," Cancer, vol. 101, no. 1, pp. 77-82, Jul. 1, 2004.

[10] W. K. Kelly et al., "Randomized, double-blind, placebo-controlled phase III trial comparing docetaxel and prednisone with or without bevacizumab in men with metastatic castration-resistant prostate cancer: CALGB 90401," J Clin Oncol, vol. 30, no. 13, pp. 1534-40, May 1, 2012.

[11] C. K. Choi, J. B. Kim, E. H. Jang, Y. N. Youn, and W. H. Ryu, "Curved biodegradable microneedles for vascular drug delivery," Small, vol. 8, no. 16, pp. 2483-8, Aug. 20, 2012.

[12] D. W. Miles et al., "Phase III study of bevacizumab plus docetaxel compared with placebo plus docetaxel for the first-line treatment of human epidermal growth factor receptor 2-negative metastatic breast cancer," J Clin Oncol, vol. 28, no. 20, pp. 3239-47, Jul. 10, 2010.

[13] K. Miller et al., "Paclitaxel plus bevacizumab versus paclitaxel alone for metastatic breast cancer," N Engl J Med, vol. 357, no. 26, pp. 2666-76, Dec. 27, 2007.

[14] J. Lehmann et al., "Adjuvant cisplatin plus methotrexate versus methotrexate, vinblastine, epirubicin, and cisplatin in locally advanced bladder cancer: results of a randomized, multicenter, phase III trial (AUO-AB 05/95)," J Clin Oncol, vol. 23, no. 22, pp. 4963-74, Aug. 1, 2005.

[15] A. F. Okines et al., "Bevacizumab with peri-operative epirubicin, cisplatin and capecitabine (ECX) in localised gastro-oesophageal adenocarcinoma: a safety report," Ann Oncol, vol. 24, no. 3, pp. 702-9, March 2013.

[16] N. J. Robert et al., "RIBBON-1: randomized, double-blind, placebo-controlled, phase III trial of chemotherapy with or without bevacizumab for first-line treatment of human epidermal growth factor receptor 2-negative, locally recurrent or metastatic breast cancer," J Clin Oncol, vol. 29, no. 10, pp. 1252-60, Apr. 1, 2011.

[17] A. Sandler et al., "Paclitaxel-carboplatin alone or with bevacizumab for non-small-cell lung cancer," N Engl J Med, vol. 355, no. 24, pp. 2542-50, Dec. 14, 2006.

[18] C. S. Fuchs et al., "Ramucirumab monotherapy for previously treated advanced gastric or gastro-oesophageal junction adenocarcinoma (REGARD): an international, randomised, multicentre, placebo-controlled, phase 3 trial," Lancet, vol. 383, no. 9911, pp. 31-39, Jan. 4, 2014.

[19] H. Wilke et al., "Ramucirumab plus paclitaxel versus placebo plus paclitaxel in patients with previously treated advanced gastric or gastro-oesophageal junction adenocarcinoma (RAINBOW): a double-blind, randomised phase 3 trial," Lancet Oncol, vol. 15, no. 11, pp. 1224-35, October 2014.

[20] J. Holash et al., "VEGF-Trap: a VEGF blocker with potent antitumor effects," Proc Natl Acad Sci USA, vol. 99, no. 17, pp. 11393-8, Aug. 20, 2002.

[21] J. Tabernero et al., "Ramucirumab versus placebo in combination with second-line FOLFIRI in patients with metastatic colorectal carcinoma that progressed during or after first-line therapy with bevacizumab, oxaliplatin, and a fluoropyrimidine (RAISE): a randomised, double-blind, multicentre, phase 3 study," Lancet Oncol, vol. 16, no. 5, pp. 499-508, May 2015.

[22] L. G. Paz-Ares et al., "Treatment outcomes by histology in REVEL: A randomized phase III trial of Ramucirumab plus docetaxel for advanced non-small cell lung cancer," Lung Cancer, vol. 112, pp. 126-133, October 2017.

[23] N. Ogawa et al., "Clinical significance of platelet derived growth factor-C and -D in gastric cancer," Oncol Lett, vol. 10, no. 6, pp. 3495-3501, December 2015.

[24] R. Erber et al., "Combined inhibition of VEGF and PDGF signaling enforces tumor vessel regression by interfering with pericyte-mediated endothelial cell survival mechanisms," FASEB J, vol. 18, no. 2, pp. 338-40, February 2004.

[25] R. K. Jain, "Transport of molecules across tumor vasculature," Cancer Metastasis Rev, vol. 6, no. 4, pp. 559-93, 1987.

[26] K. Pietras et al., "Inhibition of platelet-derived growth factor receptors reduces interstitial hypertension and increases transcapillary transport in tumors," Cancer Res, vol. 61, no. 7, pp. 2929-34, Apr. 1, 2001.

[27] K. Pietras et al., "Inhibition of PDGF receptor signaling in tumor stroma enhances antitumor effect of chemotherapy," Cancer Res, vol. 62, no. 19, pp. 5476-84, Oct. 1, 2002.

[28] T. J. Perren et al., "A phase 3 trial of bevacizumab in ovarian cancer," N Engl J Med, vol. 365, no. 26, pp. 2484-96, Dec. 29, 2011.

[29] M. Reck et al., "Phase III trial of cisplatin plus gemcitabine with either placebo or bevacizumab as first-line therapy for nonsquamous non-small-cell lung cancer: AVAil," J Clin Oncol, vol. 27, no. 8, pp. 1227-34, Mar. 10, 2009.

[30] E. Van Cutsem et al., "Addition of aflibercept to fluorouracil, leucovorin, and irinotecan improves survival in a phase III randomized trial in patients with metastatic colorectal cancer previously treated with an oxaliplatin-based regimen," J Clin Oncol, vol. 30, no. 28, pp. 3499-506, Oct. 1, 2012.

[31] N. S. Vasudev and A. R. Reynolds, "Anti-angiogenic therapy for cancer: current progress, unresolved questions and future directions," Angiogenesis, vol. 17, no. 3, pp. 471-94, July 2014.

[32] H. Verdaguer, J. Tabernero, and T. Macarulla, "Ramucirumab in metastatic colorectal cancer: evidence to date and place in therapy," Ther Adv Med Oncol, vol. 8, no. 3, pp. 230-42, May 2016.

[33] O. Gunnarsson, N. R. Pfanzelter, R. B. Cohen, and S. M. Keefe, "Evaluating the safety and efficacy of axitinib in the treatment of advanced renal cell carcinoma," Cancer Manag Res, vol. 7, pp. 65-73, 2015.

[34] K. Zirlik and J. Duyster, "Anti-Angiogenics: Current Situation and Future Perspectives," Oncol Res Treat, vol. 41, no. 4, pp. 166-171, 2018.

What is claimed is:

1. A method for treating a proliferative disorder comprising administering to a subject a therapeutically effective amount of crenolanib or salt thereof in combination with a vascular endothelial growth factor (VEGF), a vascular endothelial growth factor receptor (VEGFR), or both (VEGF/VEGFR) inhibitor that is not axitinib sufficient to treat the proliferative disorder.

2. The method of claim 1, wherein the proliferative disorder is at least one of: biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, uterine cancer, or other tumors.

3. The method of claim 1, wherein the therapeutically effective amount of crenolanib or a salt thereof is from about 50 mg to 500 mg per day, 100 to 450 mg per day, 200 to 400 mg per day, 300 to 500 mg per day 350 to 500 mg per day, or 400 to 500 mg per day.

4. The method of claim 1, wherein the therapeutically effective amount of crenolanib or salt thereof, the VEGF/VEGFR inhibitor, or both, is administered at least one of continuously, intermittently, systemically, or locally.

5. The method of claim 1, wherein the therapeutically effective amount of crenolanib or salt thereof, the VEGF/VEGFR inhibitor, or both, is administered orally, intravenously, or intraperitoneally.

6. The method of claim 1, wherein crenolanib is crenolanib besylate, crenolanib phosphate, crenolanib lactate, crenolanib hydrochloride, crenolanib citrate, crenolanib acetate, crenolanib toluenesulfonate, and crenolanib succinate.

7. The method of claim 1, further comprising providing the subject a chemotherapeutic agent that comprises one or more of alkylating agents, antimetabolites, natural products, or a combination thereof.

8. The method of claim 7, wherein the chemotherapeutic agent is provided in a therapeutically effective amount and is selected from:

an alkylating agent that comprises one or more of carmustine, chlorambucil, cyclophosphamide, ifosfamide, lomustine, streptozotocin, temozolomide, cisplatin, carboplatin, nedaplatin, or oxaliplatin;

an anti-proliferative agent that comprises one or more of vinblastine, vinorelbine, vincristine, vindesine, vinflunine, paclitaxel, docetaxel, cabazitaxel, etoposide, teniposide, topotecan, irinotecan, doxorubicin, epirubicin, valrubicin, mitoxantrone, bleomycin, estramustine, or mitomycin; or an antimetabolite that comprises one or more of methotrexate, pemetrexed, raltitrexed, fluorouracil, floxuridine, capcitabine, or gemcitabine.

9. The method of claim 8, wherein a therapeutically effective amount of the alkylating agent is from about 22 mg to 40 mg every 6 weeks, 150 to 200 mg every 6 weeks, 4 to 20 mg per day for 3 to 6 weeks, 2,000 to 4,750 given over 5 days, 4 to 19 mg per day, 1.44 to 3.12 g per day for 5 days in 3 weeks, 150 to 340 mg every 6 weeks, 600 to 1,300 mg per day for 5 days within 6 weeks, 90 to 390 mg daily, 24 to 260 mg per day for 5 days within 6 weeks, 240 to 1,690 mg every 6 weeks, 72 to 234 mg every 4 weeks 78 to 221 mg every 2 weeks.

10. The method of claim 8, wherein a therapeutically effective amount of the antimetabolite is from about 3.6 to 7.8 mg, 12 to 1,300 mg, 600 to 1,300 mg on day 1 of 21-day cycles.

11. The method of claim 8, wherein the therapeutically effective amount of the chemotherapeutic agent is administered at least one of continuously, intermittently, systemically, or locally.

12. The method of claim 8, wherein the therapeutically effective amount of the chemotherapeutic agent is from about 0.48 mg to 3.7 mg, 7.2 mg to 28.9 mg, 30 mg to 78 mg, 96 mg to 455 mg, 72 mg to 260 mg, 400 mg to 760 mg every three weeks; 42 to 260 mg given days 1, 3, 5 of 21 day cycle, 198 mg to 650 mg once weekly, 0.9 mg to 3.9 mg daily for 5 days of 21 day cycle, 150 mg to 910 mg daily for 5 days of 21 day cycle, 48 mg to 195 mg every 21 days, 90 mg to 312 mg once every 3 or 4 weeks, 800 mg once weekly every 6 weeks, 14.4 mg to 36.4 mg every 21 days, 12.5 units to 47.5 units every 1 to 2 weeks, 500 mg to 1,520 mg per day, 12 mg to 52 mg every 6 to 8 weeks.

13. The method of claim 1, wherein the VEGF/VEGFR inhibitor that is not axitinib is selected from at least one of: ramucirumab, bevacizumab, ranibizumab, aflibercept, HLX12, ziv-aflibercept, vanucizumab, TX16, UB-922, BEVZ92, BCD-021, BI695502, CHS-5217, JHL1149, FKB238, Abevmy, ONS1045, PF06439535, HD204, SB8, TAB008, RPH001, BP102, HLX04, CT-P16, IBI305, LY01008, Mvasi, apagen, CHS-3351, PF582, Xlucane, FYB201, razumab, CHS-2020, FYB203, ABP-201, sevacizumab, brolucizumab, CSL346, faricimab, hPV19, TAB014, UB-924, VGX-100, VX70, STI-A0168, CVX-241, BI 836880, ABT-165, conbercept, MP0250, MP0260, angiocal, abicipar pegol, anlotinib, apatinib, altiratinib, vandetanib, linifanib, motesanib, necuparanib, HLX12, APX004, CDP791, HLX-06, IBI302, icrucumab, IMC-1C11, IMC-3C5, MSB0254, navicixizumab, tanibirumab, V-DOS47, cabozantinib, brivanib, dovitinib lactate, famitinib, foretinib, fruquintinib, golvatinib, henatinib, ponatinib, lenvatinib, lucitanib, sorafenib, nintedanib, orantinib, pegdinetanib, cediranib, rivoceranib, midostaurin, sitravatinib, regorafenib, sunitinib, sulfatinib, tesevatinib, tivozanib, vatalanib, or pazopanib.

14. The method of claim 1, wherein the therapeutically effective amount of the VEGF/VEGFR inhibitor that is not axitinib is from about 250 mg to 1,425 mg every two to three weeks, 400 mg to 2,600 mg every two to three weeks, 40 mg to 475 mg every two weeks.

15. The method of claim 1, wherein the therapeutically effective amount of crenolanib, VEGF/VEGFR inhibitor that is not axitinib and a pharmaceutical agent, are administered from at least one of:

for as long as the subject needs treatment for the proliferative disorder;

one or more times a day or more for as long as the subject is in need of treatment for the proliferative disorder;

for a patient with a newly diagnosed proliferative disorder or the proliferative disorder has progressed on at least one line of chemotherapy in the advanced setting; or up to three times a day for as long as the subject is in need of treatment of the proliferative disorder.

16. A method for dual inhibition of angiogenesis by inhibition of both PDGFR and VEGFR signaling as a treatment of a proliferative disorder in a subject comprising a composition comprising a therapeutically effective amount of a VEGF/VEGFR inhibitor that is not axitinib, and a therapeutically effective amount of crenolanib or pharmaceutically acceptable salt thereof, wherein the subject is a human subject.

17. The method of claim 16, wherein the proliferative disorder is at least one of: biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, uterine cancer, or other tumors.

18. The method of claim 16, wherein the therapeutically effective amount of crenolanib or a salt thereof is from about 50 mg to 500 mg per day, 100 to 450 mg per day, 200 to 400 mg per day, 300 to 500 mg per day 350 to 500 mg per day, or 400 to 500 mg per day.

19. The method of claim 16, further comprising a pharmaceutical agent comprises one or more of paclitaxel, docetaxel, 5-fluorouracil, irinotecan, leucovorin calcium, oxaliplatin, capecitabine, interferon alpha, temozolomide, carboplatin, pegylated liposomal doxorubicin, topotecan, cisplatin, pemetrexed or a combination thereof.

20. The method of claim 16, wherein the VEGF/VEGFR inhibitor that is not axitinib comprises ramucirumab, bevacizumab, ranibizumab, aflibercept, HLX12, ziv-aflibercept, vanucizumab, TX16, UB-922, BEVZ92, BCD-021, BI695502, CHS-5217, JHL1149, FKB238, Abevmy, ONS1045, PF06439535, HD204, SB8, TAB008, RPH001, BP102, HLX04, CT-P16, IBI305, LY01008, Mvasi, apagen, CHS-3351, PF582, Xlucane, FYB201, razumab, CHS-2020, FYB203, ABP-201, sevacizumab, brolucizumab, CSL346, faricimab, hPV19, TAB014, UB-924, VGX-100, VX70, STI-A0168, CVX-241, BI 836880, ABT-165, conbercept, MP0250, MP0260, angiocal, abicipar pegol, anlotinib, apatinib, altiratinib, vandetanib, linifanib, motesanib, necuparanib, HLX12, APX004, CDP791, HLX-06, IBI302, icrucumab, IMC-1C11, IMC-3C5, MSB0254, navicixizumab, tanibirumab, V-DOS47, cabozantib, brivanib, dovitinib lactate, famitinib, foretinib, fruquintinib, golvatinib, henatinib, ponatinib, lenvatinib, lucitanib, sorafenib, nintedanib, orantinib, pegdinetanib, cediranib, rivoceranib, midostaurin, sitravatinib, regorafenib, sunitinib, sulfatnib, tesevatinib, tivozanib, valatanib, or pazopanib.

21. The method of claim 16, wherein the VEGF/VEGFR inhibitor that is not axitinib therapeutically effective amount is from about 250 mg to 1,425 mg every two to three weeks, 400 mg to 2,600 mg every two to three weeks, 40 mg to 475 mg every two weeks.

22. The method of claim 16, wherein the therapeutically effective amount of the crenolanib or a salt thereof, the VEGF/VEGFR inhibitor that is not axitinib, or both, is at least one of:
administered at least one of continuously, intermittently, systemically, or locally; administered in an amount to keep the subject in a state of stable disease, or to cause a partial response, or complete response for as long as the subject needs such treatment for the proliferative disorder; or
administered up to three times a day for as long as the subject is in need for the treatment of the proliferative disorder.

23. The method of claim 16, wherein crenolanib is crenolanib besylate, crenolanib phosphate, crenolanib lactate, crenolanib hydrochloride, crenolanib citrate, crenolanib acetate, crenolanib toluenesulfonate, or crenolanib succinate.

24. The method of claim 16, wherein the therapeutically effective amount of the composition is administered orally, intravenously, subcutaneously, or intraperitoneally.

25. The method of claim 16, further comprising the step of determining if the proliferative disorder is resistant to folinic acid, fluorouracil and oxaliplatin (FOLFOX) chemotherapy.

26. A pharmaceutical composition for treatment of a cancer in a human subject comprising: a crenolanib or salt thereof and a VEGF/VEGFR inhibitor that is not axitinib in a therapeutically effective amount for the treatment of the cancer.

27. The pharmaceutical composition of claim 26, wherein the cancer is at least one of: biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, uterine cancer, or other solid tumors.

28. The pharmaceutical composition of claim 26, wherein the crenolanib is formulated for dosing at 50 mg to 500 mg per day, 100 to 450 mg per day, 200 to 400 mg per day, 300 to 500 mg per day 350 to 500 mg per day, or 400 to 500 mg per day.

29. The pharmaceutical composition of claim 26, wherein the crenolanib is formulated to be administered continuously, intermittently, systemically, or locally.

30. The pharmaceutical composition of claim 26, wherein a therapeutically effective amount of crenolanib, VEGF/VEGFR inhibitor that is not axitinib, or both, is formulated to be administered orally, intravenously, or intraperitoneally.

31. The pharmaceutical composition of claim 26, wherein crenolanib is crenolanib besylate, crenolanib phosphate, crenolanib lactate, crenolanib hydrochloride, crenolanib citrate, crenolanib acetate, crenolanib toluenesulfonate, and crenolanib succinate.

32. The pharmaceutical composition of claim 26, further comprising a chemotherapeutic agent in an amount effective to treat the cancer, wherein the chemotherapeutic agent is selected from at least one of: one or more alkylating agents, one or more antimetabolites, one or more anti-proliferative agents, or a combination thereof.

33. The pharmaceutical composition of claim 32, wherein the chemotherapeutic agent is at least one of:
an alkylating agent that comprises one or more of carmustine, chlorambucil, cyclophosphamide, ifosfamide, lomustine, streptozotocin, temozolomide, cisplatin, carboplatin, nedaplatin, or oxaliplatin;
antimetabolite that comprises one or more of methotrexate, pemetrexed, raltitrexed, fluorouracil, floxuridine, capecitabine, or gemcitabine; or
anti-proliferative agents that comprise one or more of vinblastine, vinorelbine, vincristine, vindesine, vinflunine, paclitaxel, docetaxel, cabazitaxel, etoposide, teniposide, topotecan, irinotecan, doxorubicin, epirubicin, valrubicin, mitoxantrone, bleomycin, estramustine, or mitomycin.

34. The pharmaceutical composition of claim 26, wherein the VEGF/VEGFR inhibitor that is not axitinib comprises ramucirumab, bevacizumab, ranibizumab, aflibercept, HLX12, ziv-aflibercept, vanucizumab, TX16, UB-922, BEVZ92, BCD-021, BI695502, CHS-5217, JHL1149, FKB238, Abevmy, ONS1045, PF06439535, HD204, SB8, TAB008, RPH001, BP102, HLX04, CT-P16, IBI305, LY01008, Mvasi, apagen, CHS-3351, PF582, Xlucane, FYB201, razumab, CHS-2020, FYB203, ABP-201, sevacizumab, brolucizumab, CSL346, faricimab, hPV19, TAB014, UB-924, VGX-100, VX70, STI-A0168, CVX-241, BI 836880, ABT-165, conbercept, MP0250, MP0260, angiocal, abicipar pegol, anlotinib, apatinib, altiratinib, vandetanib, linifanib, motesanib, necuparanib, HLX12, APX004, CDP791, HLX-06, IBI302, icrucumab, IMC-1C11, IMC-3C5, MSB0254, navicixizumab, tanibirumab, V-DOS47, cabozantib, brivanib, dovitinib lactate, famitinib, foretinib, fruquintinib, golvatinib, henatinib, ponatinib, lenvatinib, lucitanib, sorafenib, nintedanib, orantinib, pegdinetanib, cediranib, rivoceranib, midostaurin, sitravatinib, regorafenib, sunitinib, sulfatnib, tesevatinib, tivozanib, valatanib, or pazopanib.

* * * * *